United States Patent

Tsuk

[11] 4,010,196
[45] Mar. 1, 1977

[54] LINEAR POLYESTER SALTS
[75] Inventor: Andrew G. Tsuk, Plattsburg, N.Y.
[73] Assignee: American Home Products Corporation, New York, N.Y.
[22] Filed: June 25, 1975
[21] Appl. No.: 590,357
[52] U.S. Cl. .............................. 260/484 A; 424/78
[51] Int. Cl.² ......................................... C07L 69/66
[58] Field of Search ............................... 260/484 A
[56] References Cited
FOREIGN PATENTS OR APPLICATIONS
567,237   2/1945   United Kingdom ........... 260/484 A Primary Examiner—Paul J. Killos
Attorney, Agent, or Firm—Stephen Venetianer

[57] ABSTRACT

Polyester salts of the formula

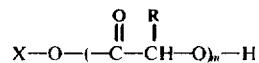

wherein X is an alkali metal, hydrogen or a combination of the two; R is methyl or hydrogen and m has a value from about 3 to about 30. These novel linear polyester salts find utility as absorbable matrix materials for depot drug dosage forms.

4 Claims, No Drawings

LINEAR POLYESTER SALTS

BACKGROUND OF THE INVENTION

1. Field of the Invention

This invention relates to novel linear polyester salts and to their use as a matrix material for medicaments that useful in human beings and warm-blooded animals.

2. Description of Prior Art

There are numerous publications that disclose combinations of polymers and drugs designed to give sustained or delayed release of the drugs when these drugs are taken orally. The oral route has as a major drawback when used in conjunction with a sustained release formulation in that body fluids will permeate the polymer part of the formulation in causing swelling and breaking of the protective coating and thus releasing the drug in its entirety. Recently U.S. Pat. No. 3,773,919 disclosed the use of a polylactide in combination with drugs which was then introduced under the skin of a warm-blooded animal to produce a sustained release effect. The polymers used in U.S. Pat. No. 3,773,919 were of a high molecular weight and presented several drawbacks. Namely, the formulation described in this patent produced slow absorption rates in the body, produced formulations of high viscosity which made the admixture of drugs difficult to handle and the high melting points of the admixture made the use of certain heatsensitive drugs impossible. Conversely, low molecular weight polyesters have been tacky semi-solids or syrups, which are difficult to handle. They also have a relatively high acid number which poses problems of tissue irritiation.

DESCRIPTION OF THE INVENTION

It has now been found that the compositions defined by this invention are of relatively low molecular weight and yet are hard, brittle and non-tacky solids which are perfectly suitable for use in formulations of absorbable depot dosage forms. This result is surprising in that U.S. Pat. No. 3,755,558 teaches that the higher molecular weight polyesters even as high as 32,000 molecular weight are slightly tacky and thus not suitable for formulations. The present invention consists of a lower molecular weight polyester salt which posseses suitable absorption rates while overcoming the difficulties encountered with higher molecular weight polyesters. Additionally, the sodium and/or potassium salts of this invention overcome the above-described acidity problem.

The novel linear polyester salts of this invention can be represented by the formula:

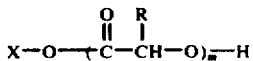

wherein X is an alkali metal, hydrogen or a mixture of both; R is methyl or hydrogen and the average value of m is from about 3 to about 30 with the proviso that at least 20% of X is an alkali metal and at least 20% of R is methyl. The novel salts are soluble in most organic solvents such as chloroform, acetone, DMF, DMSO, ethyleneglycolmonoethylacetate, carbontetrachloride, tetrahydrofuran, MEK, N,N,Diethylactamide, diethyleneglycolmonoethylether and dioxane.

The novel linear polyester salts of this invention can be prepared from polymers or copolymers prepared essentially in the manner described in U.S. Pat. No. 2,362,511 which is herein incorporated by reference. Useful polymers or copolymers which can be converted into the novel salts of this invention are prepared from material containing from about 20% to about 100% lactic acid and from about 0% to about 80% glycolic acid. To the resulting polymer or copolymer anhydrous sodium carbonate is added and the mixture is heated for about two days at about 90° C. Additional chain ends are generated by the by-product water through hydrolysis of the polymer. The resulting novel salts have a molecular weight of less than 2000 and a melting point of 60°-70° C.

These novel linear polyester salts find particular use as an absorbable matrix material for drugs. Any drug that is stable up to 80° C can be incorporated into the molten liquid of the novel salts of this invention.

Typical drugs which can be administered by means of this invention are, for example, peptides such as the LH-FSH releasing hormone, somatostatin, pentagastrin, oxytocin, insulin and related compounds, isosorbide-2-mononitrate, isosorbide dinitrate, pentaerythritol nitrates, nitroglycerin and the like, prostaglandins and prostaglandin analogues, major and minor tranquilizers, anti-depressants, cardiontonics, testosterone and other androgens and derivatives, progesterone and other progestins and derivatives, natural estrogens and derivatives, ergot alkaloids and derivatives, colchicine, and propranolol and other anti-adrenergics. Further typical drugs are isoproterenol, phenylephrine and other adrenergics; hydrocortisone, prednisone, triamcinolone and other adrenocorticoids; acetanimophen, codeine, propoxyphene and other analgesics; antidiarrheals; apomorphine, atropine, morphine and other alkaloids; buclizine, cyclizine, prochlorperazine and other antiemetics; hydralazine, methyldopa and other antihypertensives; sedatives and hypnotics; enzymes; antibacterials, antimicrobials; nutritional agents; heparin and other anticoagulants. Up to 70% by weight of the drug based on the weight of the polymer can be incorporated into the novel matrix material.

The drug and the novel polyester salt of this invention can be mixed by any number of known methods. One preferred method is to heat the matrix material until it becomes molten, add the drug, cool and then suspend the resulting mixture in a pharmaceutical acceptable carrier, such as peanut oil. This procedure is suitable for injection. Other acceptable methods for preparing and administering the above-type formulation includes dissolving the matrix material in PEG 200, 300, or 400, adding the drug and injecting. Implantation of pellets into subcutaneous cellular tissue or muscular tissue also produces an acceptable sustained release dosage form. The novel salts find particular use as a matrix material for the compound having the formula (butaclamol U.S. Pat. No. 3,657,250).

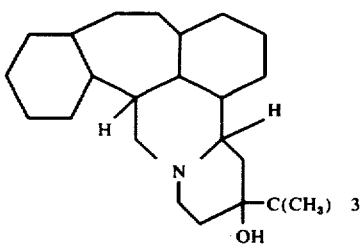

This particular compound is useful as a central nervous system depressant, anti-convulsant and as an anti-inflammatory.

Butaclamol is mixed into the molten polyester salts of this invention. The butaclamol contained therein constitutes a weight percent of up to about 70% of the mixture. The mixture can be subdivided and incorporated into dosage forms.

The following examples illustrate the preparation of the novel compounds of this invention.

EXAMPLE 1

A copolymer of equal molar amounts of glycolic and lactic acids was prepared essentially according to the procedure of U.S. Pat. No. 2,362,511. The resulting tacky semi-solid had an acid number of 0.564 milliequivalents per gram. To 500 g. of this was added 21g. of anhydrous $Na_2CO_3$, and the mixture was maintained at 123°-128° C for 42 hours, with occasional stirring. The $Na_2CO_3$ was completely dissolved. The water generated by the reaction between the polyester and $Na_2CO_3$ was used up in the process through hydrolysis of some of the ester bonds, which was evidenced by the fact that the final product still had an acid number of 0.25 milliequivalents per gram. This value, together with the sodium content, which corresponded to 0.783 milliequivalents per gram, represent the carboxyl chain ends, and thus the number of moles of polyester per gram. Further calculations from the above values show that for this product X is 76% Na and 24% H, $m$ has the value of 14.3, and R is 50% $CH_3$ and 50% H. The product is a clear, light amber, brittle and nontacky solid. It is soluble in most common organic solvents to form solutions of low viscosity. Upon heating, it gradually softens and becomes liquid at temperatures below 70° C.

EXAMPLE 2

The procedure of Example 1 was followed, except that only lactic acid was used. To 792 g. of a colorless polylactic acid syrup, with an acid number of 2.09 milliequivalents per gram, 100 g. of anhydrous $Na_2CO_3$ was added, and the mixture was maintained for several days at 90°-100° C, with occasional stirring. As in Example 1, additional chain ends were generated from the by product water through hydrolysis, and the final acid number was 0.731 milliequivalents per gram. Assay of the sodium content gave 5.05% by weight, or 2.20 milliequivalents per gram, which correspond to 75% of the total carboxyl end groups of 2.931 milliequivalents per gram. Further calculations give a value of 4.3 for m. In this case, R is $CH_3$ and X is 75% Na of 25% H. The product is colorless, and similar to the product of Example 1 in all other aspects.

EXAMPLE 3

Pure crystalline glycollic acid, 351 grams (4.5 moles), USP lactic acid (85%), 131 milliliters (1.5 moles), and 774 milliliters of distilled water were introduced into a resin kettle equipped with a nitrogen inlet bubbling tube, thermometer heating mantle, condenser and receiver. Under a slow stream of nitrogen, water was distilled off under atmospheric pressure until the pot temperature reached about 180° C and the distillation was then continued under aspirator vacuum until the pot temperature reached 219° C, a total distillation time of about 12 hours. The acid number of the cooled solid melt was 0.543 milliequivalents carboxyl per gram of product, indicating a molecular weight of 18.0. To this was added 18.0 grams of $Na_2CO_3$ as in Example 1 and X=90%. R=25% methyl, 75% hydrogen, M=16.

EXAMPLE 4

Pure crystalline glycolic acid, 217 grams (2.8 moles), USP lactic acid (85%), 105 milliliters (1.2 moles), and 394 milliliters of distilled water were introduced into the resin kettle as in Example 3, and water was distilled off under atmospheric pressure until the pot temperature reached about 180° C and the distillation was then continued under aspirator vacuum until the pot temperature reached 205° C, a total distillation time of about 10 hours. The acid number of the cooled solid melt was 0.819 milliequivalents carboxyl per gram of product, indicating a molecular weight of 1200. 8.3 gms of $Na_2CO_3$ was added as in Example 1 and X=55%. R=30% methyl, 70% hydrogen, M=14.

EXAMPLE 5

Glycolic acid in aqueous solution, 570 milliliters containing 465 grams of acid (6.0 moles), USP lactic acid (85%), 140 milliliters (1.6 moles), and 470 milliliters of distilled water were introduced into the resin kettle as in Example 3, and water was distilled off under atmospheric pressure until the pot temperature reached about 180° C and the distillation was then continued under aspirator conditions until the pot temperature reached 255° C, a total distillation time of about 16 hours. The acid number of the cooled solid melt was 0.670 milliequivalents carboxyl per gram of product indicating a molecular weight of 1500. 16.3 grams of $Na_2CO_3$ was added and X=65%. R=21% methyl, 79% hydrogen, M=16.

EXAMPLE 6

Glycolic acid in aqueous solution, 314 milliliters containing 794 milligrams per milliliter (3.4 moles) by titration, USP lactic acid (85%), 190 milliliters (2 moles), and 300 milliliters of distilled water were introduced into the resin kettle as in Example 3 and water was distilled off under atmospheric pressure until the pot temperature reached about 180° C and the distillation was then continued under aspirator conditions until the pot temperature reached 210° C, a total of about 16 hours. The acid number of the cooled solid melt was 0.81 milliequivalents carboxyl per gram of product, indicating a molecular weight of 1200. To this was added 21.9 grams of $Na_2CO_3$ as in Example 1 and X=85%. R=37% methyl, 63% hydrogen and M=11.

EXAMPLE 7

The procedure of Example 1 was followed except that only lactic acid was used. To 67.3 grams of a colorless polyactic acid syrup with an acid number of 1.49 in milliequivalents per gram was added 8.3 grams of powdered anhydrous potassium carbonate. This was maintained in an oil bath at 125° C. for about 8 hours with occasional stirring. The resulting clear solid had an acid number of 0.68 milliequivalents per gram. It was soluble in common organic solvents but not in water. When broken up into small pieces, the solid remained free flowing at room temperature. It was slightly tacky to the touch indicating a softening point close to body temperature. In this case R is methyl and x is 71% K and 29% H. The value of M is 5.2.

The lithium salts can be made in a similar manner. Lithium, however, is toxic so that such salts can not be used for drug dosage forms in humans.

Another aspect of this invention are the magnesium salts of the polyesters as illustrated in the following Example:

EXAMPLE 8

To 67.3 grams of colorless polyactic acid syrup of the previous example was added 2.4 grams of powdered magnesium oxide. The mix was maintained in an oil both at 125° C for about 8 hours with occasional stirring. During this time the mixture thickened noticeably turning milky. Upon cooling, the product is a milky non-tacky solid soluble in common organic solvent but not in water. The nature of this product is complex because magnesium can form salts with one or two carboxyl groups and only the second salt yields water as a by-product. Therefor the degree neutralization and the degree of polymerization cannot be calculated from available data. Titration with base in nonaqueous media gave two end points at 0.51 and 1.75 milliequivalents per gram respectively.

Similarly, magnesium salts can be made employing from 0.2 to 2 moles of magnesium per mole of polyester.

Attempts to prepare the calcium salts employing the same polyester as in this Example 8 (67.3 grams, 0.1 mole) and calcium carbonate (6.0 grams, 0.06 mole) were unsuccessful at temperatures up to 200° C apparently due to the insolubility of the calcium carbonate in the polyester syrup.

Organic bases such as ethylenediamine, although soluble in the polyester, did not result in solidification.

The linear polyester salts of this invention are especially useful in preparing dosage forms for the treatment of bovine mastitis. Copending application, Ser. No. 590,358 of Gerald L. Reuter and Andrew G. Tsuk filed on even date herewith and incorporated herein by reference describes and claims solid dosage forms for the treatment of bovine mastitis comprising from about 30 to 70% by weight of the dosage form of at least one antimicrobial agent intimately dispersed in a polyester, the polyester having a molecular weight less than 2,000, a glycolic acid content of about 60 to 80 mol per cent, and a lactic acid content of about 20 to 40 mole per cent. Broad spectrum antibiotics such as chlortetracycline, oxytetracycline and tetracycline are the preferred microbial agents. The linear polyester salts of this invention can be substituted for the polyesters of the above identified copending application in all respects and with equivalent results.

I claim:

1. Polyester salts having the formula:

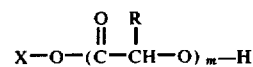

wherein X is an alkali metal, hydrogen or a mixture of both; R is methyl or hydrogen and the average value of m is from about 3 to about 30 with the proviso that at least 20% of X is an alkali metal and at least 20% of R is methyl.

2. Polyester salts according to claim 1 wherein the alkali metal is sodium.

3. Polyester salts according to claim 1 wherein the alkali metal is potassium.

4. Magnesium salts of polyesters having a molecular weight less than 2000 a glycolic acid content of 0 to 80 mole per cent and a lactic acid content of about 20 to 100%.